United States Patent [19]

Krämer et al.

[11] Patent Number: 4,788,215
[45] Date of Patent: Nov. 29, 1988

[54] HALOGENOHYDROXYFLAVONES

[75] Inventors: Josef Krämer, Seeheim-Jugenheim; Klaus Irmscher, Darmstadt; Helmut Prücher, Heppenheim; Rolf-Dieter Hesch, Hanover-Kleefeld, all of Fed. Rep. of Germany

[73] Assignee: Merck Patent Gesellschaft mit Beschränkter Haftung, Darmstadt, Fed. Rep. of Germany

[21] Appl. No.: 98,584

[22] Filed: Sep. 18, 1987

Related U.S. Application Data

[62] Division of Ser. No. 801,703, Nov. 26, 1985, Pat. No. 4,713,465.

[30] Foreign Application Priority Data

Nov. 26, 1984 [DE] Fed. Rep. of Germany ....... 3443007
Feb. 19, 1985 [DE] Fed. Rep. of Germany ....... 3505611

[51] Int. Cl.⁴ ..................... A61K 31/35; C07D 311/30
[52] U.S. Cl. ..................... 514/456; 549/403; 549/220; 514/100
[58] Field of Search ............... 549/403, 220; 514/456, 514/100

[56] References Cited

U.S. PATENT DOCUMENTS 3,433,805  3/1969  Krämer et al. ............... 549/403
3,450,717  6/1969  Krämer et al. ............... 549/403
3,462,455  8/1969  Krämer et al. ............... 549/403

Primary Examiner—Nicky Chan
Attorney, Agent, or Firm—Millen & White

[57] ABSTRACT

Halogenohydroxyflavones

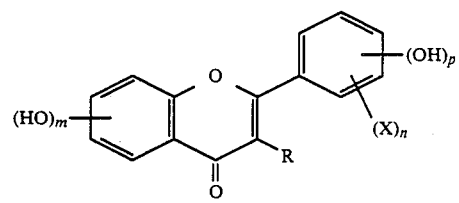

I in which
R is alkyl having 1-3 C atoms,
X is F, Cl, Br or I, and
m, n and p are each 1, 2 or 3, and their esters with sulfuric acid and phosphoric acid, and the salts of these compounds, are suitable for the treatment of hyperthyroidism.

12 Claims, No Drawings

HALOGENOHYDROXYFLAVONES

This is a division of application Ser. No. 801,703 filed Nov. 26, 1985, now U.S. Pat. No. 4,713,465.

The invention relates to new flavone derivatives.

SUMMARY OF THE INVENTION

It is an object of this invention to provide new compounds having valuable properties, in particular those which can be used for the preparation of medicaments.

Upon further study of the specification and appended claims, further objects and advantages of this invention will become apparent to those skilled in the art.

These objects have been achieved by providing flavones of formula I

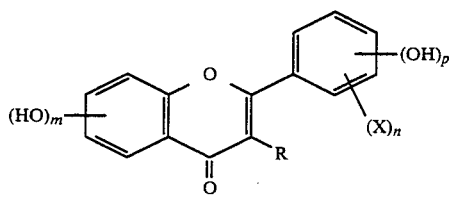

in which
R is alkyl having 1-3 C atoms,
X is F, Cl, Br or I, and
m, n and p are each 1, 2 or 3, and to their esters with sulfuric acid ("I-sulfates") and phosphoric acid ("I-phosphates"), and to the salts of these compounds.

Detailed Discussion

It has been found that the compounds of the formula I, their sulfates, phosphates and the salts of these compounds have valuable pharmacological properties. Thus, they are able, for example, to inhibit thyroxine 5'-deiodase and they exhibit considerable potency in the treatment of hyperthyroidism; they are able to exert a selective effect on the thermogenic action of the thyroid hormones. In addition, they exhibit antibacterial and antitrichomonal as well as antimutagenic and thus anticarcinogenic actions. Furthermore, they prolong the action potential of heart cells and thus exert an antiarrhythmic action.

The compounds of the formula I, their sulfates, phosphates and the salts of these compounds can thus be used as active compounds in medicaments in human and veterinary medicine. The flavones I themselves, and the I-sulfates and I-phosphates are also used as intermediates, in particular for the preparation of the said salts.

In the formula I R is preferably methyl, but is also ethyl, propyl or isopropyl. X is preferably Br, but is also Cl or I, as well as F. The parameters m and p are both preferably 1, but are also 2 or 3; the parameter n is preferably 2, and 1 is also preferred, but it is also 3. Thus the compounds of the formula I are, in general, mono-, di- or tri-halogeno-di-, -tri-, -tetra-, -penta- or -hexa-hydroxyflavones, preferably dihalogenodihydroxyflavones, in particular dibromodihydroxyflavones, but also difluorodihydroxyflavones, dichlorodihydroxyflavones, diiododihydroxyflavones, monobromomonochlorodihydroxyflavones, monobromomonoiododihydroxyflavones, monobromomonofluorodihydroxyflavones, monochloromonoiododihydroxyflavones or monochloromonofluorodihydroxyflavones. The hydroxyl groups in the benzo ring of the chromone system are preferably in the 6-position, but also in the 5-, 7- and/or 8-position, and those in the phenyl ring are preferably in the 4'-position, but also in the 2'- and/or 3'-position. Specifically, those which are particularly preferred are the 3',5'-dihalogeno-6,4'-, -5,4'-, -7,4'- and -8,4'-dihydroxyflavones, for example the 3',5'-dibromo-, and the 3',5'-difluoro-, 3',5'-dichloro-, 3',5'-diiodo-6,4'-, -5,4'-, -7,4'- and -8,4'-dihydroxyflavones, and the 3'-halogeno-6,4'-, -5,4'-, -7,4'- and -8,4'-dihydroxyflavones, for example the 3'-bromo-, and the 3'-fluoro-, 3'-chloro-, 3'-iodo-6,4'-, -5,4'-, -7,4'- and -8,4'-dihydroxyflavones of the formula I, in all cases especially those where R=methyl.

Accordingly, the invention particularly relates to those compounds of the formula I, and their sulfates, their phosphates and the salts of these compounds, in which at least one of the said radicals and/or parameters has one of the preferred meanings indicated above and/or is located in one of the positions indicated as being preferred. Some preferred groups of compounds can be expressed by the part formulae Ia to If below, which correspond to the formula I and in which the radicals which are not defined in detail have the meanings indicated for formula I but in which

| in Ia | m and p | are each 1 and |
|---|---|---|
|  | n | is 1 or 2; |
| in Ib | m and p | are each 1, and |
|  | n | is 2; |
| in Ic | m and p | are each 1, |
|  | n | is 2, and |
|  | R | is methyl; |
| in Id | m and p | are each 1, |
|  | n | is 2, |
|  | R | is methyl, and |
|  | X | is Br or I; |
| in Ie | m and p | are each 1, and |
|  | n | is 2, |
|  | the OH group in the phenyl ring being in the 4'-position, and the two X atoms being in the 3'- and 5'-positions; | |
| in If | m and p | are each 1, |
|  | n | is 2, |
|  | R | is methyl, and |
|  | X | is Br or I, |
|  | the OH group in the phenyl ring being in the 4'-position, and the two X atoms being in the 3'- and 5'-positions. | |

The invention also relates to a process for the preparation of compounds of the formula I, and of their esters with sulfuric acid and phosphoric acid, and the salts of these compounds, characterized in that a compound of the formula II

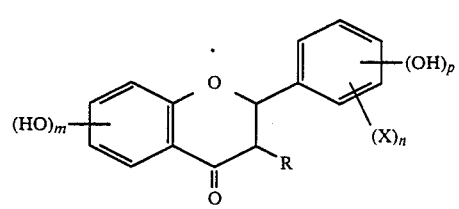

in which R, X, m, n and p have the meanings indicated above, is treated with a dehydrogenating agent, or in that a compound of the formula III

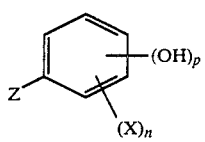

in which Z is

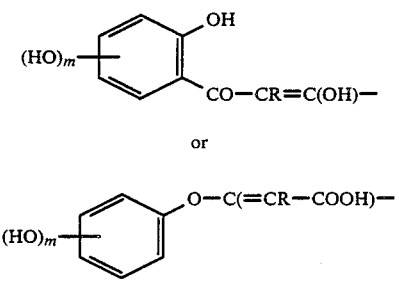

and R, X, m, n and p have the meanings indicated above, or a reactive derivative of a compound of this type, is cyclized, or in that a compound which corresponds to the formula I but in place of one or more H atoms contains one or more solvolyzable or hydrogenolyzable group(s) is treated with a solvolyzing or hydrogenolyzing agent, and/or in that a compound of the formula I is esterified with sulfuric acid, phosphoric acid or a derivative of these acids which is suitable for esterification, and/or in that a compound of the formula I, or one of its esters with sulfuric acid or phosphoric acid, is converted into a salt by treatment with a base.

The compounds of the formula I are, moreover, prepared by methods which are known per se and are as described in the literature (for example in standard works such as Houben-Weyl, Methoden der Organischen Chemie (Methods of Organic Chemistry) published by Georg Thieme, Stuttgart; Organic Reactions, John Wiley & Sons, Inc., New York), and specifically under reaction conditions which are known and suitable for the said reactions. In this context, it is also possible to make use of variants which are known per se but which are not mentioned in detail here.

The term "dehydrogenating agent" is, according to the invention, to be understood in a relatively wide sense. Examples of suitable agents are halogens, such as chlorine, bromine or iodine, N-haloamides, selenium dioxide, hydrogen peroxide, dehydrogenating catalysts, such as palladium, preferably in the presence of a hydrogen acceptor, halogenated quinones, such as chloranil and 2,3-dichloro-5,6-dicyanoquinone, and pyridinium bromide perbromide and other substances which generate active halogen. The dehydrogenation can be carried out in one step or in several steps.

It is possible for the preparation of the flavone derivatives of the formula I to treat the flavanones II themselves with dehydrogenating agents. However, it is also possible not to isolate the flavanones II as the pure substances but merely to generate them in situ. For example, it is possible to use a ketone (chalcone) of the formula IV

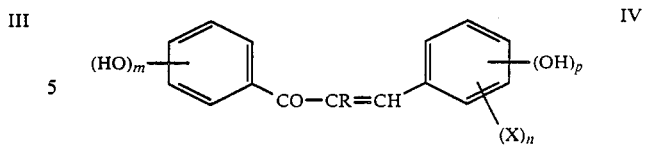

in which R, X, m, n and p have the meaning indicated above, it also being possible for phenolic hydroxyl groups to be in a protected form, in place of the flavanones II in the reaction. This entails the flavanones II being formed as intermediates.

The chalcones or flavanones are preferably obtained by condensation of an appropriate alkyl phenyl ketone with an appropriate halogenohydroxyaldehyde, or by Friedel-Crafts or Hoesch synthesis from an appropriate polyhydric phenol and a reactive derivative of a halogenohydroxycinnamic acid.

Furthermore, it is possible to carry out the process in such a manner that the ketone IV is not isolated either but is only generated in situ. For example, it is possible to react the alkyl phenyl ketone with the halogenohydroxyaldehyde and to allow one of the said dehydrogenating agents to act on the reaction mixture. For the dehydrogenation it is possible, for example, to treat the flavanones II with halogens, preferably with chlorine or bromine, and then to eliminate hydrogen halide. If the process starts from the ketones IV then the intermediates produced are the chalcone dihalides, which by the action of basic agents, preferably methanolic or ethanolic sodium or potassium hydroxide, lose 2 moles of hydrogen halide and simultaneously cyclize to give the flavones. It is also possible in this reaction for the phenolic OH group in the 2-position of the ketone IV to be in a protected form, for example as an ester group or as a tetrahydropyranyl ether group; the hydroxyl group can be liberated by the action of acids or alkalis. If the process starts from a flavanone II then the reaction sequence can include a 3-haloflavanone step. For example, it is possible to introduce a halogen atom in the 2- or 3-position of the flavanone derivative II by bromination with the action of light. The dehydrohalogenation of the resulting 2- or 3-haloflavanone is carried out with, for example, alcoholic alkali, for example aqueous/ethanolic potassium hydroxide, or by the action of tertiary amines, such as collidine, lutidine, pyridine or picoline, or with lithium chloride or bromide and lithium carbonate in dimethylformamide, preferably at temperatures between about 0° and about 100°.

Another method of dehydrogenation comprises the reaction of the ketone IV or flavanone II with selenium dioxide, preferably at elevated temperature in a high-boiling solvent, such as xylene, amyl alcohol or acetic anhydride. If acetic anhydride is used then intermediate protection of phenolic hydroxyl groups is unnecessary. Otherwise, it is better to carry out the reaction with protected, for example esterified, hydroxyl groups.

Another dehydrogenating agent is hydrogen peroxide in alkaline solution. If a chalcone is used as the starting material then the reaction takes place via the epoxide and the 3-hydroxyflavanone. It is preferably carried out in an aqueous, aqueous/alcoholic or alcoholic, for example methanolic, solution and at room temperature, but also with cooling at the start of the reaction.

Another method is the dehydrogenation of the flavanones with palladium in the presence of a hydrogen acceptor. Acceptors which are preferably used as unsaturated acid derivatives, such as cinnamic acid, maleic anhydride or similar compounds. This reaction is preferably carried out in the presence of an inert solvent, such as water, and between 50° and 120°, for example.

It is also possible to obtain the flavones of the formula I by cyclization of a ketone of the formula III in which Z has the meaning indicated above under (a), it also being possible for it to be in the corresponding diketo form. This cyclization can be carried out by, for example, heating with glycerol for several hours, preferably under nitrogen, the action of acids, such as concentrated hydrochloric acid, hydrobromic acid, hydroiodic acid, sulfuric acid, phosphoric acid, acetic acid, formic acid or mixtures thereof, preferably at temperatures between about 20° and 150°.

The ketones which are used as starting materials need not be isolated in the reaction. They can be obtained by, for example, reaction of an appropriate polyhydroxyacylophenone with a halogenohydroxybenzoic ester under the conditions customary for ester condensation.

It is also possible to obtain the flavones I by cyclization of a carboxylic acid of the formula III in which Z has the meaning indicated above under (b). This can be carried out by, for example, the action of acetyl chloride/sulfuric acid, phosphorus oxychloride or polyphosphoric acid, or by conversion into the appropriate acid halide, for example with thionyl chloride, followed by intramolecular Friedel-Crafts acylation, for example in the presence of aluminum chloride. It is also possible to use appropriate esters under hydrolyzing conditions for the cyclization.

The said carboxylic acids can be obtained, for example, by reaction of an appropriate phenol with an α-(halogenohydroxybenzoyl)-fatty acid ester (Simonis reaction); it is unnecessary to isolate the carboxylic acid in this case.

It is also possible to obtain compounds of the formula I by treatment with a solvolyzing or hydrogenolyzing agent of a compound which corresponds to the formula I but which in place of one or more H atoms contains one or more solvolyzable or hydrogenolyzable group(s).

Examples of suitable solvolyzable, preferably hydrolyzable groups, are ester or ether groups, such as O-alkanoyl, for example acetoxy; O-aroyl, for example benzoyloxy; O-alkyl, for example methoxy or ethoxy; or tetrahydropyranyloxy. For example, it is possible to hydrolyze esterified or etherified hydroxyl groups in basic, neutral or acid medium. O-Alkyl groups can be cleaved by, for example, heating with HBr or HI in acetic acid. Cleavage of benzyloxy groups can also be carried out by hydrogenolysis, for example using hydrogen on a noble metal catalyst, such as Pd-charcoal, at temperatures between 0° and 100° and under pressures between about 1 and 100 bar, in an inert solvent.

The I-sulfates and I-phosphates can be obtained preferably by esterification of a compound of the formula I with sulfuric acid, phosphoric acid or a derivative of these acids which is suitable for esterification. Depending on the conditions and the number of OH groups present in I, it is possible to obtain I-mono-, -di-, -tri-, -tetra-, -penta- or -hexa-sulfates or -phosphates.

In addition to the free sulfuric and phosphoric acids, acid derivatives suitable for the reaction are, in particular, sulfamic acid, chlorosulfonic acid, sulfur trioxide and its adducts with dioxane, pyridine, dimethylaniline or diethylaniline or other tertiary bases; pyrophosphoric acid, polyphosphoric acid, phosphorus pentoxide, phosphorus oxychloride, monochlorophosphoric acid (mixture of orthophosphoric acid and phosphorus oxychloride), monobenzyl phosphate, dibenzyl phosphoric chloride, mono(2-cyanoethyl) phosphate, and phosphoric dimorpholide chloride.

The esterification of the halogenohydroxyflavone of the formula I is carried out in the absence or presence of an additional solvent. Suitable solvents which are preferred are organic bases, such as pyridine, triethylamine, quinoline, dimethylaniline and diethylaniline, if an acid, for example hydrochloric acid, is eliminated in the reaction. Otherwise, or in addition, it is possible to use inert organic solvents such as, for example, diethyl or diisopropyl ether, tetrahydrofuran, dioxane, chloroform, methylene chloride, trichloroethylene, dimethylformamide, dimethyl sulfoxide, benzene, toluene, xylene, tetralin or acetonitrile. Mixtures of the abovementioned bases and/or solvents can also be used. It is also possible to allow the reaction to take place in an excess of the esterifying agent. The reaction temperatures are between −80° and +200°, preferably between −10° and +100°.

It is possible quite generally to use for the preparation of the I-sulfates, the I-phosphates and their salts the processes described in Houben-Weyl, loc. cit., Volume VI/2, pages 452–464, and Volume XII/2, pages 143–210 (1964).

It is possible in the preparation of the compounds of the formula I, their sulfates or their phosphates, for intermediates which contain protective groups to be produced. These can be removed by hydrolysis or hydrogenolysis. In particular, it is possible to liberate protected hydroxyl groups by alkaline or careful acid hydrolysis. Such protected hydroxyl groups can be derived from the flavanoid component but are preferably derived from the sulfuric acid or phosphoric acid component of the esterification reaction. If, for example, the esterification has been carried out with mono(2-cyanoethyl) phosphate, diphenyl phosphoric chloride or phosphoric dimorpholide chloride, then the resulting phosphoric diesters or triesters or monoester diamides can be cleaved using, for example, alkali metal or ammonium hydroxide solutions, or basic or acid ion exchangers to give the desired phosphoric esters of the flavanoid. It is possible to eliminate protective groups, preferably benzyl groups in phosphoric esters, by hydrogenolysis, for example by catalytic hydrogenation, preferably under mild conditions, for example using a palladium catalyst, such as palladium on charcoal, calcium carbonate or strontium carbonate, and at room temperature and under atmospheric pressure, it being preferable for the hydrogenation to be discontinued after the calculated amount of hydrogen has been taken up.

The halogenohydroxyflavones of the formula I and their esters with sulfuric acid and phosphoric acid can be converted into the relevant salts by treatment with a base. Suitable salts are the phenolates of the halogenohydroxyflavones I, but especially the salts of the I-sulfates and I-phosphates.

Physiologically acceptable salts are preferred. The salts are, as a rule, prepared at room temperature, the solvent which is used preferably being water, alcohols such as methanol or ethanol, mixtures of water with alcohols, or the bases used for the salt formation. Suitable bases which are preferred are the hydroxides, carbonates or alcoholates of the alkali metals and alkaline earth metals, as well as the corresponding ammonium compounds, preferably sodium, potassium, calcium or magnesium hydroxide, sodium, potassium, calcium or magnesium carbonate, sodium, potassium, calcium or magnesium bicarbonate, sodium, potassium, calcium or magnesium methylate, ethylate, isopropylate or tert.-butylate, also ammonium hydroxide, carbonate or bicarbonate, as well as substituted ammonium hydroxides, carbonates or bicarbonates.

The invention also relates to the use of the compounds of the formula I, of their esters with sulfuric acid and phosphoric acid and the salts of these compounds, for the preparation of pharmaceutical formulations, in particular by non-chemical means. For this purpose they may be converted into a suitable dosage form together with at least one solid, liquid or semi-liquid vehicle or auxiliary and, where appropriate, combined with one or more other active compound(s).

The invention also relates to pharmaceutical formulations containing at least one compound of the formula I, and/or one of its esters with sulfuric acid, and/or one of its esters with phosphoric acid, and/or a physiologically acceptable salt of one of these compounds.

These formulations can be used as medicaments in human or veterinary medicine. Suitable vehicles are organic or inorganic substances which are suitable for enteral (for example oral) or parenteral administration and which do not react with the new compounds, for example water, vegetable oils, benzyl alcohols, polyethylene glycols, glycerol triacetate, gelatin, carbohydrates such as lactose or starch, magnesium stearate, talc or vaseline. Tablets, coated tablets, capsules, syrups, solutions or drops, in particular, are used for oral administration, suppositories are used for rectal administration, and solutions, suspensions, emulsions or implants are used for parenteral administration. It is also possible for the new compounds to be freeze-dried and the resulting lyophilizates to be used, for example, for the preparation of products for injection. The specified formulations can be sterilized and/or contain auxiliaries, such as lubricants, preservatives, stabilizing and/or wetting agents, emulsifiers, salts to affect the osmotic pressure, buffer substances, colorants, flavorings and/or aromatic substances. If desired, they can also contain one or more other active compounds.

The invention also relates to the use of the compounds of the formula I, of their esters with sulfuric acid, esters with phosphoric acid and/or the physiologically acceptable salts of these compounds, for controlling diseases, in particular hyperthyroidism, and to their use for the therapeutic treatment of the human or animal body. As a rule, this entails the administration of the substances according to the invention in analogy to known thyroid depressants which are commercially available, for example thiamazole, preferably in doses of about 1 to about 500 mg, in particular 5 to 100 mg, per dosage unit. The daily dose is preferably about 0.015 to 10 mg/kg of body weight. However, the specific dose for each particular patient depends on a very wide variety of factors, for example on the efficacy of the specific compound used, on the age, body weight, general state of health, sex, on the diet, on the time and route of administration, on the rate of elimination, the medicament combination, and the severity of the particular disorder for which the therapy is applied. Oral administration is preferred.

With regard to their antiarrhythmic activity, the substances of the invention may be administered in analogy to known antiarrhythmics, for example amiodarone, preferably in doses of about 10 to 500 mg, in particular 20 to 200 mg, per dosage unit. The daily dose for this indication is preferably about 0.15 to 10, in particular about 0.3 to 3 mg/kg of body weight.

"Usual working-up" signifies: water and dichloromethane are added, the phases are separated, and the organic phase is dried over sodium sulfate and evaporated and purification is carried out by crystallization and/or chromatography on silica gel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

1.6 g of bromine in 6 ml of chloroform are added dropwise to a solution of 4.12 g of 3',5'-dibromo-6,4'-dihydroxy-3-methylflavanone (m.p. 200°–202°; obtainable by reaction of 2,5-dihydroxypropiophenone with 3,5-dibromo-4-hydroxybenzaldehyde in boiling ethanol in the presence of piperidine) in 55 ml of dioxane while stirring and irradiating (500 watt Agaphot lamp). The mixture is stirred for a further 30 minutes while cooling and irradiating, the usual working-up is carried out, and the resulting crude 3,3',5'-tribromo-6,4'-dihydroxy-3-methylflavanone is dissolved in 100 ml of ethanol. 15 ml of 10% aqueous potassium hydroxide solution are added, and the mixture is boiled for 5 minutes, cooled, poured on to ice and the usual working-up is carried out.  3',5'-Dibrom-6,4'-dihydroxy-3-methylflavone ("D") is obtained, m.p. 264°–265°.

The following are obtained analogously from the appropriate flavanones by bromination to give the corresponding 3-bromoflavanones and by dehydrobromination of the latter:

3', 5'-dibromo-5,4'-dihydroxy-3-methylflavone, m.p. 238°–242°
3', 5'-dibromo-7,4'-dihydroxy-3-methylflavone, m.p. 330° (decomposition)
3',5'-dibromo-8,4'-dihydroxy-3-methylflavone, m.p. 315°–316°
3',5'-dibromo-6,4'-dihydroxy-3-ethylflavone
3',5'-dibromo-6,4'-dihydroxy-3-propylflavone
3',5-dibromo-6,4'-dihydroxy-3-isopropylflavone
3'-fluoro-6,4'-dihydroxy-3-methylflavone
3'-chloro-6,4'-dihydroxy-3-methylflavone
3'-bromo-6,4'-dihydroxy-3-methylflavone
3'-iodo-6,4'-dihydroxy-3-methylflavone
3',5'-difluoro-6,4'-dihydroxy-3-methylflavone
3',5'-dichloro-6,4'-dihydroxy-3-methylflavone
3',5'-diiodo-6,4'-dihydroxy-3-methylflavone.

EXAMPLE 2

A mixture of 1 g of 3-(3,5-dibromo-4-hydroxyphenyl)-1-(2,5-dihydroxyphenyl)-2-methyl-2-propen-1-one (obtainable from 2,5-dihydroxypropiophenone and 3,5-dibromo-4-hydroxybenzaldehyde), 1 g of $SeO_2$ and 30 ml of isoamyl alcohol is boiled for 5 hours. After filtration the filtrate is evaporated, the usual working-up is carried out and "D" is obtained, m.p. 264°–265°.

The following are obtained analogously:

3',5'-diiodo-6,4'-dihydroxy-3-methylflavone, m.p. 252°-256°
3',5'-diiodo-5,4'-dihydroxy-3-methylflavone
3',5'-diiodo-7,4'-dihydroxy-3-methylflavone
3',5'-diiodo-8,4'-dihydroxy-3-methylflavone
3',5'-diiodo-6,4'-dihydroxy-3-ethylflavone
3',5'-diiodo-6,4'-dihydroxy-3-propylflavone
3',5'-diiodo-6,4'-dihydroxy-3-isopropylflavone
3',5'-dichloro-6,4'-dihydroxy-3-methylflavone
3', 5'-dichloro-5,4'-dihydroxy-3-methylflavone
3', 5'-dichloro-7,4'-dihydroxy-3-methylflavone
3', 5'-dichloro-8,4'-dihydroxy-3-methylflavone
3',5'-dichloro-6,4'-dihydroxy-3-ethylflavone
3',5'-dichloro-6,4'-dihydroxy-3-propylflavone
3',5'-dichloro-6,4'-dihydroxy-3-isopropylflavone
3',5'-difluoro-6,4'-dihydroxy-3-methylflavone
3',5'-difluoro-5,4'-dihydroxy-3-methylflavone
3',5'-difluoro-7,4'-dihydroxy-3-methylflavone
3',5'-difluoro-8,4'-dihydroxy-3-methylflavone
3',5'-difluoro-6,4'-dihydroxy-3-ethylflavone
3',5'-difluoro-6,4'-dihydroxy-3-propylflavone
3',5'-difluoro-6,4'-dihydroxy-3-isopropylflavone.

EXAMPLE 3

A mixture of 1 g of 3-(3,5-dibromo-4-hydroxyphenyl)-1-(2,5-dihydroxyphenyl)-2-methyl-1,3-propanedione [obtainable by reaction of 2,5-dihydroxypropiophenone with 3,5-dibromo-4-hydroxybenzoyl chloride to give 2-(3,5-dibromo-4-hydroxybenzoyloxy)-5-hydroxypropiophenone and treatment with KOH/pyridine], 6 ml of acetic acid and 0.2 ml of $H_2SO_4$ is heated at 90° for 1 hour, then poured onto ice and the usual working-up is carried out. "D" is obtained, m.p. 264°-265°. The following are obtained analogously:
3'-bromo-6,4'-dihydroxy-3-methylflavone
3'-bromo-5,4'-dihydroxy-3-methylflavone
3'-bromo-7,4'-dihydroxy-3-methylflavone
3'-bromo-8,4'-dihydroxy-3-methylflavone
3'-bromo-6,4'-dihydroxy-3-ethylflavone
3'-bromo-6,4'-dihydroxy-3-propylflavone
3'-bromo-6,4'-dihydroxy-3-isopropylflavone
3'-fluoro-6,4'-dihydroxy-3-methylflavone
3'-fluoro-5,4'-dihydroxy-3-methylflavone
3'-fluoro-7,4'-dihydroxy-3-methylflavone
3'-fluoro-8,4'-dihydroxy-3-methylflavone
3'-fluoro-6,4'-dihydroxy-3-ethylflavone
3'-fluoro-6,4'-dihydroxy-3-propylflavone
3'-fluoro-6,4'-dihydroxy-3-isopropylflavone
3'-chloro-6,4-dihydroxy-3-methylflavone
3'-chloro-5,4'-dihydroxy-3-methylflavone
3'-chloro-7,4'-dihydroxy-3-methylflavone
3'-chloro-8,4'-dihydroxy-3-methylflavone
3'-chloro-6,4'-dihydroxy-3-ethylflavone
3'-chloro-6,4'-dihydroxy-3-propylflavone
3'-chloro-6,4'-dihydroxy-3-isopropylflavone
3'-iodo-6,4'-dihydroxy-3-methylflavone
3'-iodo-5,4'-dihydroxy-3-methylflavone
3'-iodo-7,4'-dihydroxy-3-methylflavone
3'-iodo-8,4'-dihydroxy-3-methylflavone
3'-iodo-6,4'-dihydroxy-3-ethylflavone
3'-iodo-6,4'-dihydroxy-3-propylflavone
3'-iodo-6,4'-dihydroxy-3-isopropylflavone

EXAMPLE 4

A solution of 1 g of 3',5'-dibromo-6-hydroxy-4'-mathoxy-3-methylflavone (obtainable by condensation of 2,5-dihydroxypropiophenone with 3,5-dibromo-4-methoxybenzoic anhydride) in 10 ml of acetic acid and 5 ml of 67% hydroiodic acid is boiled for 1 hour. "D" precipitates out on cooling; m.p. 264°-265°.

The other compounds mentioned in Example 1-3 can be obtained analogously by ether cleavage of the appropriate 4'-methoxy compounds

EXAMPLE 5

A mixture of 4.g oF "D", 3 g of sulfamic acid and 35 ml of pyridine is stirred at 90° for 1 hour then cooled and filtered. The filtrate is shaken with 36 ml of 12% sodium hydroxide solution. The upper pyrIdine layer is separated off, several ether washings are carried out, the resulting oil is taken up in methanol, the solution is treated with active charcoal, evaporated and the disodium salt of 3,5'-dibromo-6,4'-dihydroxy-3-methylflavone 6-sulfate is obtained, m.p.>325°.

The following are obtainable analogously:
3',5'-dibromo-5,4'-dihydroxy-3-methylflavone 5-sulfate di-Na salt
3',5',5'-dibromo-7,4'-dihydroxy-3-methylflavone 7-sulfate di-Na salt
3',5'-dibromo-8,4'-dihydroxy-3-methylflavone 8-sulfate di-Na salt.

EXAMPLE 6

A solution of 4.1 g of "D" in 50 ml of pyridine is added within 10 minutes to a solution of 10 ml of $POCl_3$ in 100 ml of pyridine at 0°. After standing for 15 hours, the mixture is stirred into ice/hydrochloric acid, and the mixture is heated at 95° for 1 hour, cooled, extracted with ethyl acetate, and the extract is washed with dilute hydrochloric acid and dried over $Na_2SO_4$. 3',5'-Dibromo6,4'-dihydroxy-3-methylflavone 6-phosphate is obtained by concentration of the extract, m.p. 258°-260°.

The following are obtainable analogously:
3',5'-dibromo-5,4'-dihydroxy-3-methylflavone 5-phosphate
3',5'-dibromo-7,4'-dihydroxy-3-methylflavone 7-phosphate
3',5'-dibromo-8,4'-dihydroxy-3-methylflavone 8-phosphate.

The examples which follow relate to pharmaceutical formulations which contain compounds of the formula I or their physiologically acceptable salts:

EXAMPLE A

Tablets

A mixture of 1 kg of "D", 4 kg of lactose, 1.2 kg of potato starch, 0.2 kg of talc and 0.1 kg of magnesium stearate is compressed to form tablets in a customary manner so that each tablet contains 10 mg of active compound.

EXAMPLE B

Coated tablets

Tablets are compressed in analogy to Example A and then coated in a customary manner with a coating of sucrose, potato starch, talc, tragacanth and colarant.

EXAMPLE C

Capsules 10 kg of "D" are packed in a customary manner into hard gelatin capsules so that each capsule contains 20 mg of active compound.

EXAMPLE D

Ampoules

A solution of 1 kg of 3,5'-dibromo-6,4'-dihydroxy-3-methylflavone 6-sulfate Na salt in 30 l of double-distilled water is sterilized by filtration, dispensed into ampoules, freeze-dried under sterile conditions, and closed sterile. Each ampoule contains 10 mg of active compound.

Tablets, coated tablets, capsules or ampoules which contain one or more of the other active compounds of the formula I and/or their physiologically acceptable salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A halogenohydroxyflavone of the formula

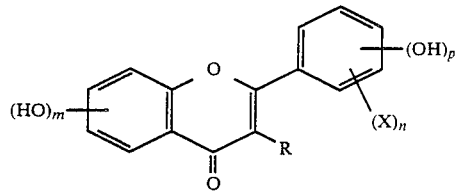

wherein
R is alkyl of 1–3 C atoms,
X is F, Cl, Br or I, and
each of m, n and p is 1, 2 or 3, or an ester thereof with sulfuric acid or phosphoric
acid, or a physiologically acceptable salt thereof.

2. 3',5'-Dibromo-6,4'-dihydroxy-3-methylflavone, a compound of claim 1.

3. A compound of claim 1, wherein m and p are each 1 and n is 1 or 2.

4. A compound of claim 1, wherein m and p are each 1, and n is 2.

5. A compound of claim 1, wherein m and p are each 1, n is 2, and R is methyl.

6. A compound of claim 1, wherein m and p are each 1, n is 2, R is methyl, and X is Br or I.

7. A compound of claim 1, wherein m and p are each 1, n is 2, the OH group in the phenyl ring is in the 4'-position, and the two X atoms are in the 3'- and 5'-positions.

8. A compound of claim 1, wherein m and p are each 1, n is 2, R is methyl, X is Br or I, the OH group in the phenyl ring is in the 4'-position, and the two X atoms are in the 3'- and 5'-positions 9. A compound of claim 1, wherein the group(s) $(HO)_m$ are in the 5, 6 or 7-position, and $(OH)_p$ is in the 4'-position.

10. A composition comprising a compound of claim 1, and a pharmaceutically acceptable carrier.

11. A composition of claim 10, wherein the amount of said compound is 1–500 mg.

12. A composition of claim 10, wherein said compound is 3',5'-dibromo-6,4'-dihydroxy-3-methylflavone.

* * * * *